(12) United States Patent
Murray et al.

(10) Patent No.: US 7,972,344 B2
(45) Date of Patent: Jul. 5, 2011

(54) SUTURE PASSING INSTRUMENT AND METHOD OF PASSING SUTURE

(75) Inventors: R. Pepper Murray, Bountiful, UT (US); Robert M. Weber, Chino Hills, CA (US)

(73) Assignee: Arthrex, Inc., Naples, FL (US)

( * ) Notice: Subject to any disclaimer, the term of this patent is extended or adjusted under 35 U.S.C. 154(b) by 718 days.

(21) Appl. No.: 12/030,782

(22) Filed: Feb. 13, 2008

(65) Prior Publication Data

US 2008/0208221 A1 Aug. 28, 2008

Related U.S. Application Data (60) Provisional application No. 60/900,993, filed on Feb. 13, 2007.

(51) Int. Cl.
*A61B 17/04* (2006.01)
(52) U.S. Cl. ...................................................... 606/144
(58) Field of Classification Search .................. 606/139, 606/144, 148, 207
See application file for complete search history.

(56) References Cited

U.S. PATENT DOCUMENTS

| | | | | |
|---|---|---|---|---|
| 4,957,498 A | * | 9/1990 | Caspari et al. | 606/146 |
| 5,947,982 A | * | 9/1999 | Duran | 606/139 |
| 6,896,686 B2 | | 5/2005 | Weber | |
| 2002/0103493 A1 | | 8/2002 | Thal | |
| 2003/0065337 A1 | | 4/2003 | Topper et al. | |
| 2003/0233106 A1 | | 12/2003 | Dreyfuss | |
| 2005/0288690 A1 | | 12/2005 | Bourque et al. | |

FOREIGN PATENT DOCUMENTS

EP 1 498 075 A1 1/2005

* cited by examiner

*Primary Examiner* — Julian W Woo
*Assistant Examiner* — Son Dang
(74) *Attorney, Agent, or Firm* — Dickstein Shapiro LLP (57) ABSTRACT

An apparatus and method for passing suture(s) in tissue repair and/or other mini-open procedures. The apparatus includes a pair of jaws mounted on a distal end of a shaft, a hand assembly mounted on a proximal end of the shaft, and a needle mounted on the hand assembly and through a cannulation of the shaft. The pair of jaws includes a lower jaw and an upper jaw, the upper jaw being curve-shaped to enable grasping of thick tissue. The hand assembly has a finger lever with a ratchet and a releaser with a hook, the hand assembly being designed to move the needle from a first position to a second position.

4 Claims, 14 Drawing Sheets

SUTURE PASSING INSTRUMENT AND METHOD OF PASSING SUTURE

CROSS REFERENCE TO RELATED APPLICATIONS

This application claims priority to U.S. Provisional Application No. 60/900,993, filed on Feb. 13, 2007, the entire disclosure of which is hereby incorporated by reference.

BACKGROUND OF THE INVENTION

1. Field of the Invention

The present invention relates to surgical instruments and, more specifically, to a suture passing instrument and a method of passing suture in arthroscopic tissue repair procedures and/or mini-open procedures.

2. Description of the Related Art

Both open and endoscopic surgical procedures often require sutures to ligate, join or otherwise treat tissue. Generally, suture needles with attached suture strands are grasped either manually or by forceps and passed through the desired work site so a knot can be tied. While the procedures are fairly uncomplicated in open surgery where most suture sites are readily accessible, in endoscopic procedures, where access to the work site is not readily available, the surgeon must use auxiliary devices to be able to grasp the suture strands and pass them through desired tissue.

Various instruments and techniques have been developed and are known for surgical repairs requiring the passing of sutures to distant locations. However, there is a need for an improved device and technique that enables the surgeon to pass sutures arthroscopically to an internal body part where the work site is only accessible through a small portal or cannula and it is difficult to pass sutures within the body.

There is also a need for a suture passing instrument that may operated by one-hand, provides maximum comfort and ease of use, and is ideal for single row, double row or margin convergence.

SUMMARY OF THE INVENTION

The present invention fulfills the needs noted above by providing a suture passing instrument and a method of passing sutures in arthroscopic and mini-open procedures.

The present invention includes a suture passing instrument for use in arthroscopic and mini-open procedures having a handle assembly at a proximal end and a pair of jaws (an upper jaw, and a lower jaw) at a distal end with a shaft connecting the handle assembly and the jaws. The upper jaw is pivotally connected to the lower jaw and the jaws are movable with respect to each other. The lower jaw is substantially straight with respect to the shaft while the upper jaw is curve-shaped, preferably humpback-shaped. The humpback-shaped upper jaw is designed to be parallel with the lower jaw when grasping a thick tissue.

The handle assembly includes a ratchet-like mechanism and a handle, the ratchet-like mechanism being pivotally connected to the handle. The ratchet-like mechanism consists of a finger lever with a ratchet, and a releaser with a hook, the ratchet and the hook having a plurality of teeth to engage the finger lever and the releaser.

A cannulation on a proximal end of the shaft is provided to receive a proximal end of a flexible needle. A distal end of the flexible needle is carried by the lower jaw and the needle is movable between a first position wherein the needle is substantially housed within the lower jaw and a second position wherein a distal portion of the needle protrudes from the lower jaw. The needle is moved between the first position and the second position by using the handle assembly.

The apparatus further includes a securing mechanism to secure the suture in place in the lower jaw prior to being carried by the flexible needle. The securing mechanism may include a "V" groove, a wedge, or a slot on the bottom of a distal portion of the lower jaw.

A method is provided for suturing a tissue using the suture passing instrument of the present invention. The method includes the steps of clamping a piece of tissue to be sutured using the instrument, securing a suture in place for engagement with a flexible needle, engaging the suture with the needle, releasing the instrument from a user's hand, grabbing the suture with a retriever, releasing an upper jaw of the instrument, and retrieving the suture.

An another method is provided for suturing a tissue using the suture passing instrument of the present invention. The method includes the steps of loading the needle onto the instrument, loading a suture into the lower jaw, using the finger lever to close the jaws and to advance the instrument into the subacromial space. The method includes the additional steps of opening the jaws by releasing the finger lever and grasping the desired bite of tissue, closing the jaws using the finger lever and advancing the needle and suture through the tissue, retracting the needle by disabling the ratchet from the hook, and retrieving the suture using a retriever or grasper.

These and other features and advantages of the present invention will become apparent from the following description of the invention that is provided in connection with the accompanying drawings and illustrated embodiments of the invention.

DETAILED DESCRIPTION OF THE PREFERRED EMBODIMENTS

The present invention is a method and apparatus for passing sutures in arthroscopic tissue repair procedures and/or mini-open procedures.

Figures 1A, 1B, 1C:
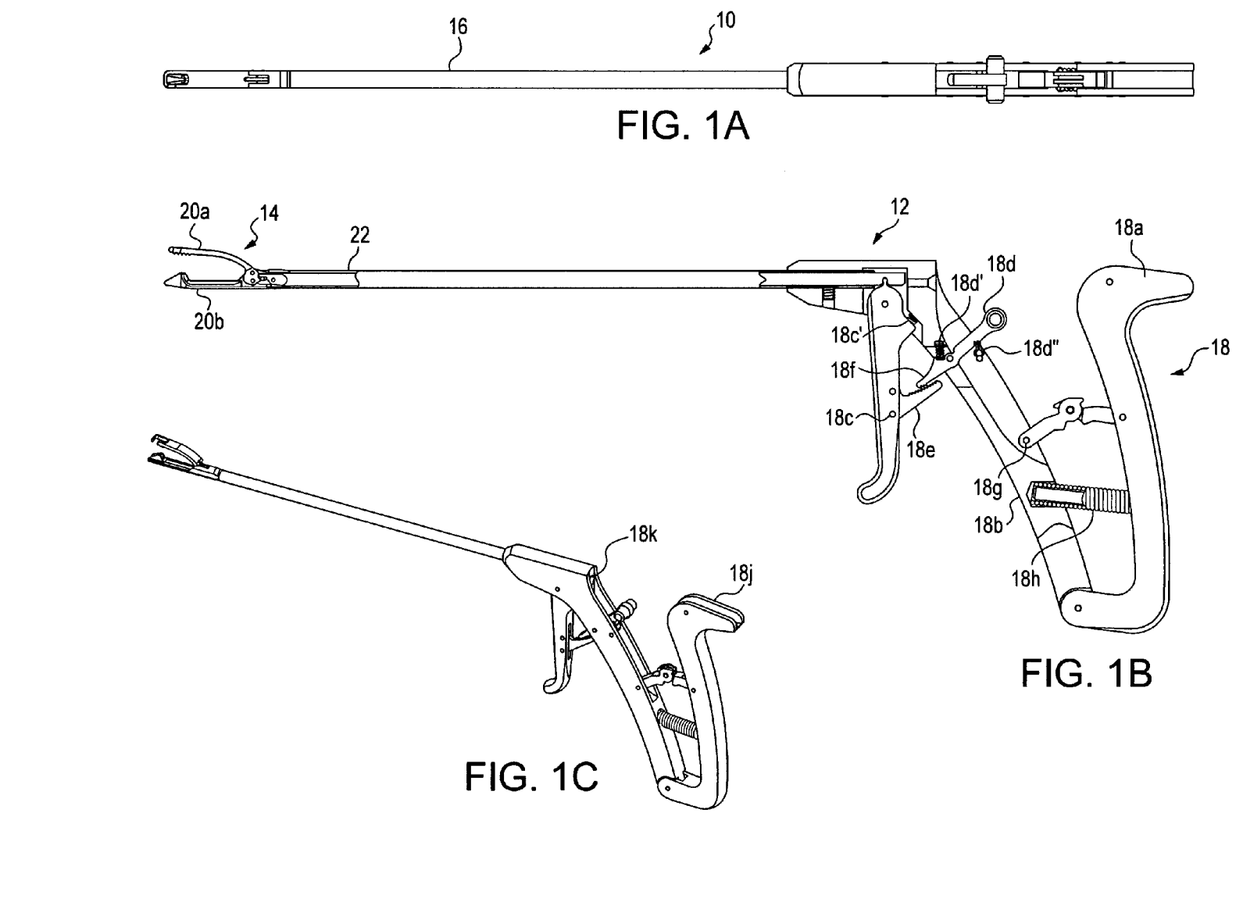
FIG. 1 illustrates front, top and perspective views of a suture passing instrument, in accordance with a first embodiment of the present invention.

Referring to FIG. 1, a first preferred embodiment of a suture passing instrument 10 according to the present invention is shown. The suture passing instrument 10 has an elongate configuration with a proximal end 12 and a distal end 14. A pair of jaws, an upper jaw 20a and a lower jaw 20b, are disposed at the distal end 14 and are coupled to a handle assembly 18 disposed at the proximal end 12 through an elongate shaft or tube 16. The shaft 16 preferably has a length of about 160 mm and a diameter of about 4.5 mm.

Figure 5A:
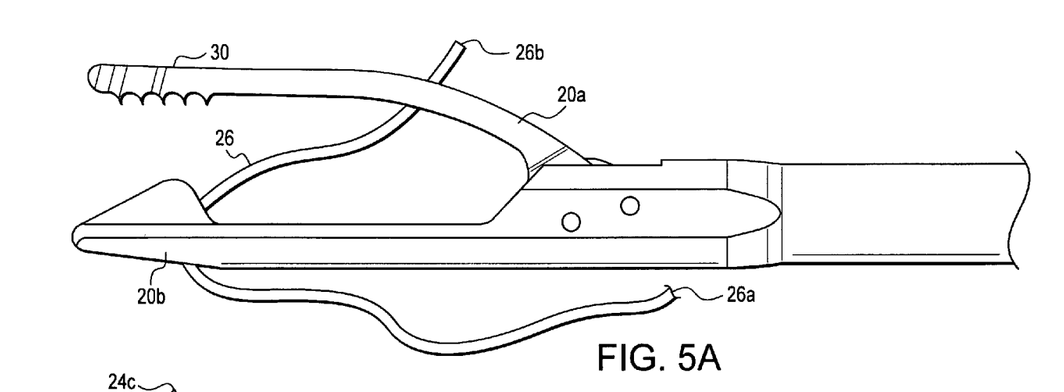
FIGS. 5A-5B illustrate side elevation views of a distal end of the suture passing instrument, in accordance with the first embodiment of the present invention.

The lower jaw 20b of the suture passing instrument 10 is substantially straight with respect to the shaft 16. The lower jaw 20b may include a "V" groove, wedge, or slot 42 (FIG. 2) on the bottom of a distal portion for receiving a suture 26 (FIG. 5). The upper jaw 20a is curve-shaped, preferably hump-back shaped, having a certain radius of curvature and is pivotally connected to the lower jaw 20b. The upper jaw 20a is designed to be parallel with the lower jaw 20b when grasping a thick tissue.

The handle assembly 18 includes a handle (not shown) having a proximal end 18a and a distal end 18b, and a ratchet-like mechanism (not shown) having a finger lever 18c with a ratchet 18e and a releaser 18d with a hook 18f. The finger lever 18c and the releaser 18d perform substantially similar to a ratchet and a pawl. The ratchet 18e and the hook 18f have a plurality of teeth to engage the finger lever 18c and the releaser 18d. The finger lever 18c and the releaser 18d are pivotally connected to the distal end 18b of the handle (not shown). The proximal and distal ends 18a, 18b of the handle (not shown) are linkably connected via a link 18g and tension between the proximal and distal ends 18a, 18b is maintained using springs 18h.

The finger lever 18c is designed to move from a first position to a second position, with a spring 18c' provided to maintain tension on the finger lever 18c and to force the finger lever 18c to go back to a default position. At its default position, the finger lever 18c is farthest from the distal end 18b of the handle.

The releaser 18d is designed to move from a first position to a second position, with a spring 18d' provided to maintain tension on the releaser 18d and to force the releaser 18d to go back to a default position. The releaser 18d further includes a portion 18d" designed to engage into a cross pin (not shown) and to securely hold the releaser 18d.

The suture passing instrument 10 further includes an actuator 22, which is provided within the shaft 16. A proximal end of the actuator 22 is pivotally connected to the finger lever 18c and a distal end of the actuator 22 is pivotally connected to the upper jaw 20a. The actuator 22 is designed to move the upper jaw 20a from a first position to a second position as the finger lever 18c is moved from a first position to a second position. At the default position of the finger lever 18c, the upper jaw 20a is farthest from the lower jaw 20b.

Figure 2:
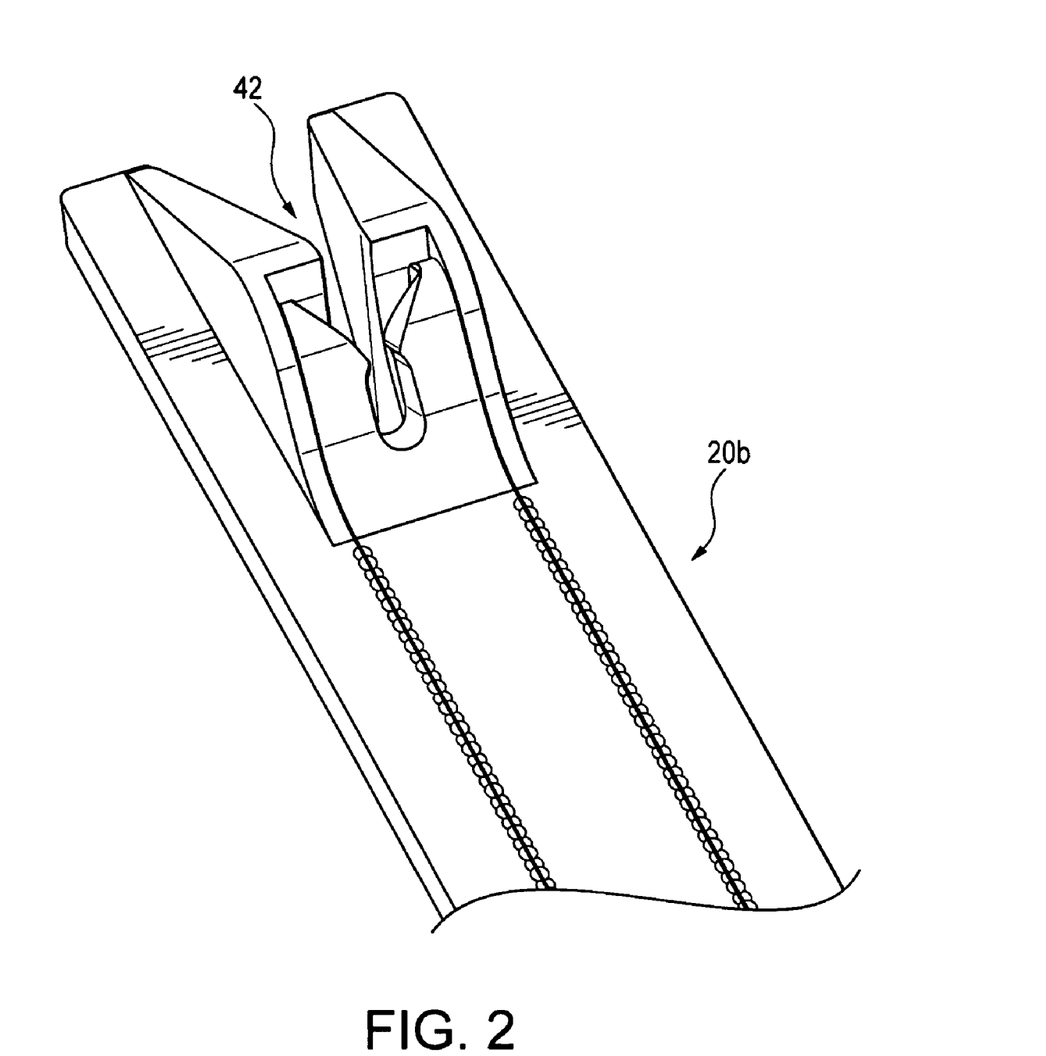
FIG. 2 illustrates a close-up, perspective view of a lower jaw of the suture passing instrument, in accordance with a first embodiment of the present invention.
Figure 3A:
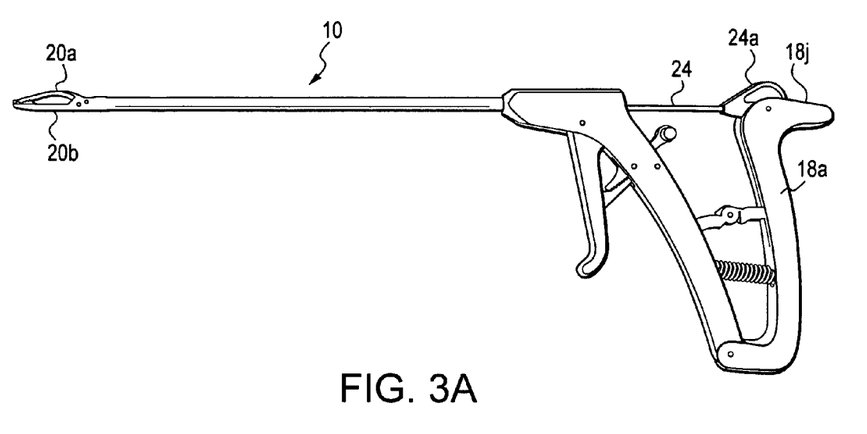
FIG. 3A illustrates a perspective view of the suture passing instrument having a needle, in accordance with the first embodiment of the present invention.

Referring to FIG. 2, the lower jaw 20b has a securing mechanism at a distal tip of the lower jaw 20b. The securing mechanism may preferably be a wedge, slot or groove, 42. The securing mechanism is formed integrally with the jaw 20b. To assemble the suture 26, a first end 26a (FIG. 5A) is held beneath the lower jaw 26b and the other end 26b (FIG. 5A) above the lower jaw 20b. The ends 26a, 26b (FIG. 5A) may be pulled in a proximal direction such that the suture 26 is wedged into the groove 42. When disposed in the groove 42, the suture 26 is securely in place for engagement by the needle 24 (FIG. 3). The suture is preferably a braided suture such as a Fiberwire™, sold by Arthrex, Inc., Naples, Fla.

Figure 3B:
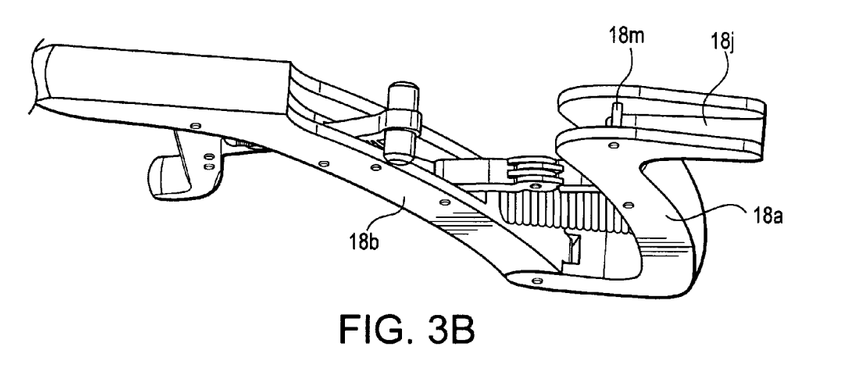
FIG. 3B illustrates a perspective view of the suture passing instrument showing a cannulation and a cross pin, in accordance with the first embodiment of the present invention.

Referring to FIGS. 3A-3B, the suture passing instrument 10 further includes a bendable needle 24, preferably formed of nitinol. Needle 24 is received in a cannulation 18k (FIG. 1) passing through the shaft 16. A slot 24f (FIG. 4B) on a proximal end 24a of the needle 24 is engaged securely into a cross pin 18m provided in a cannulation 18j on the proximal end 18a of the handle. Subsequent to securing the needle 24, the needle 24 may be moved between a first position and a second position by moving the proximal and distal ends 18a, 18b closer to each other. The needle 24 has a generally flat, narrow and elongate configuration.

Figure 4A:
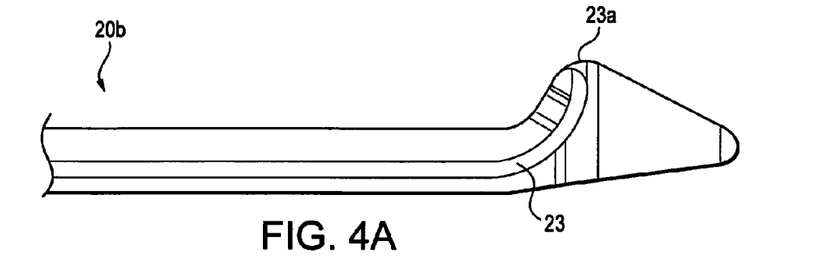
FIG. 4A illustrates a partially-removed side elevation view of the lower jaw of the suture passing instrument, in accordance with a first embodiment of the present invention.
Figure 4B:
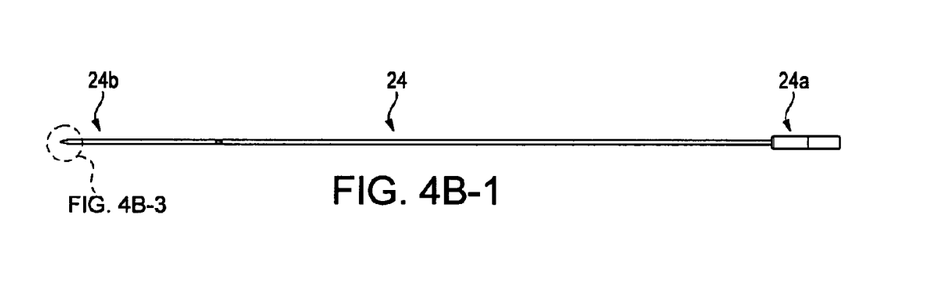
FIG. 4B illustrates a front and a top view of the needle of the suture passing instrument, in accordance with a first embodiment of the present invention.
Figure 4B:
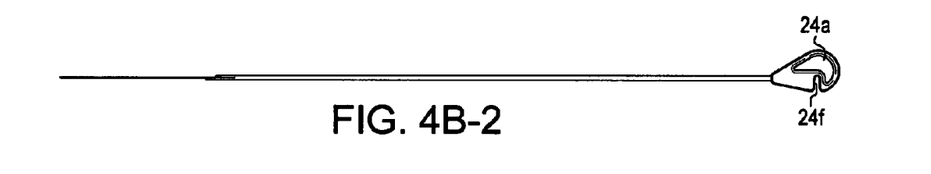
Figure 4B:
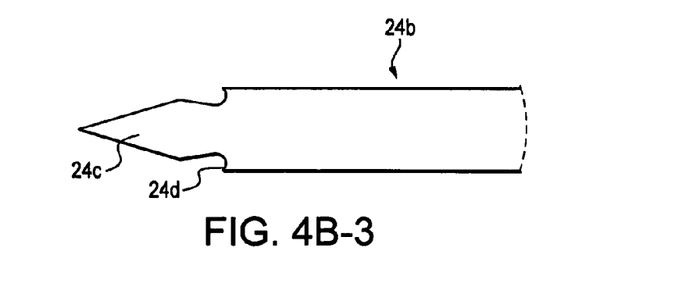

Referring now to FIGS. 4A-4B, the lower jaw 20b is configured to house the needle 24. The needle 24 is substantially disposed in a channel 23 within the lower jaw 20b when the needle 24 is in a non-operative, or non-piercing, position. In an operative position, the needle 24 is advanced distally to exit from an opening 23a in the lower jaw 20b. The needle 24 is bendable so that it can be moved generally with an axial force and can be bent on a curve, for example, 90° to move generally toward the upper jaw 20a. It is to be expressly understood that the needle 24 can be bent at any angle and advanced in any direction.

The needle 24 has a pointed tip 24c at a distal end 24b of the needle 24 and side barbs 24d provided from the pointed tip 24c. The side barbs 24d are preferably about 2 mm from the pointed tip 24c. The pointed tip 24c is designed to pierce the suture 26 (FIG. 2) and the side barbs 24d are designed to carry the suture 26 (FIG. 2).

Figure 5B:
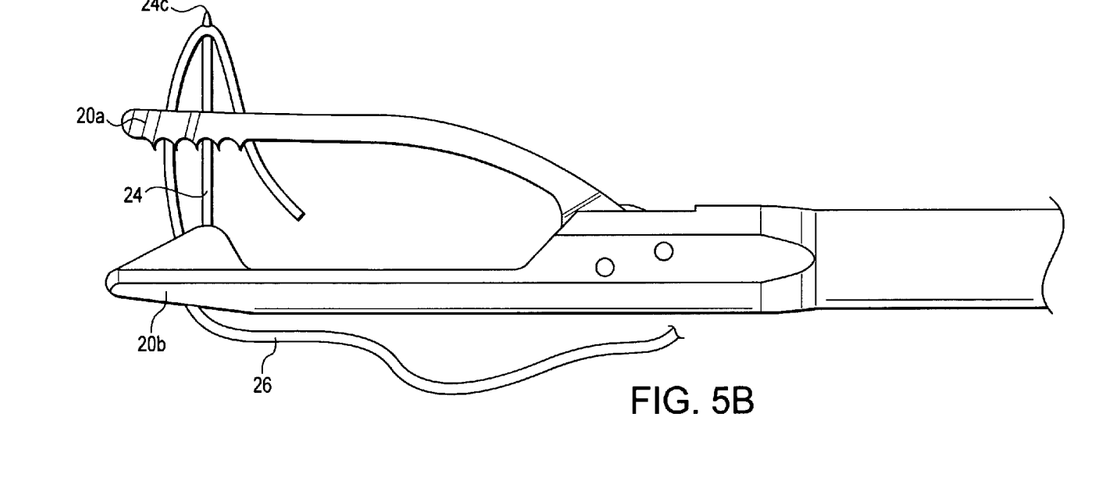

Referring to FIGS. 5A-5B, a suture 26 is secured to the lower jaw 20b. The needle 24 is distally advanced using the handle assembly 18 (FIG. 1) such that the pointed tip 24c pierces the suture 26 and carries the suture 26, exiting a channel 30 on the upper jaw 20a.

Figure 6A:
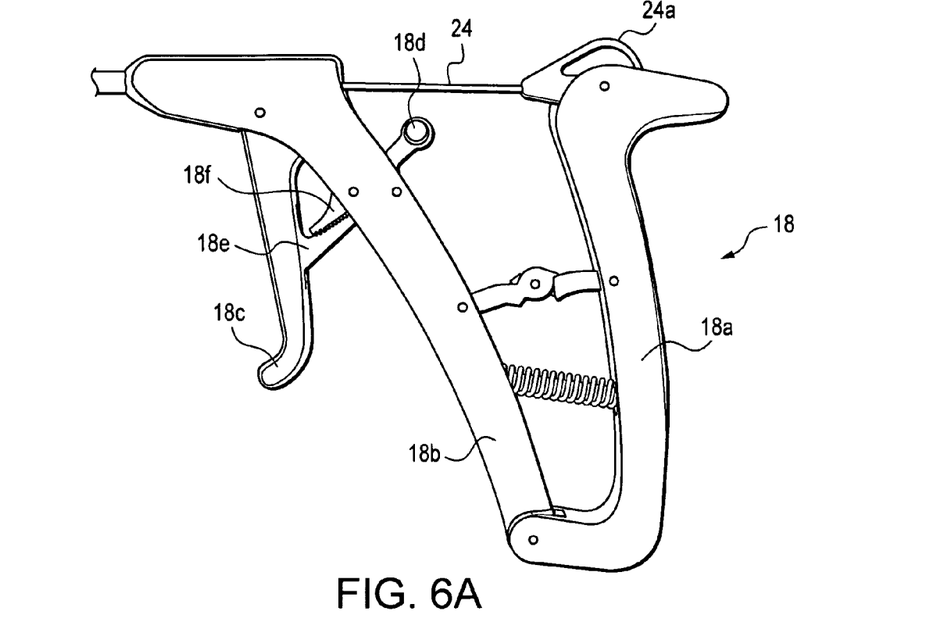
FIGS. 6A-6C illustrate a side elevation view of a proximal side and a distal side of the suture passing instrument when a ratchet of the suture passing instrument is enabled, in accordance with the first embodiment of the present invention.
Figure 6B:
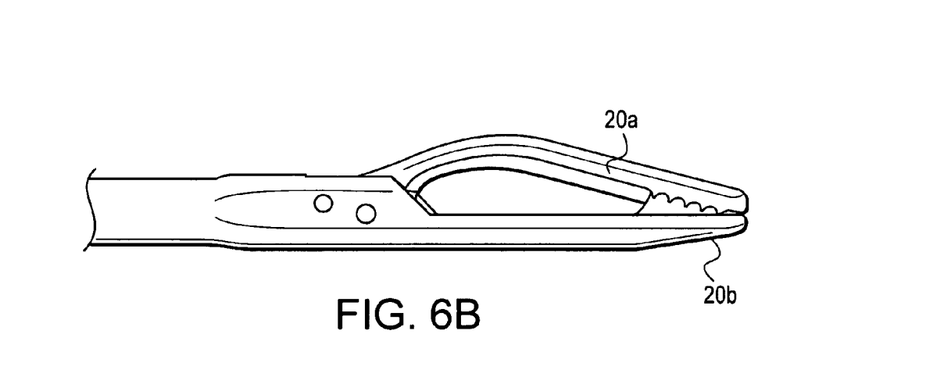
Figure 6C:
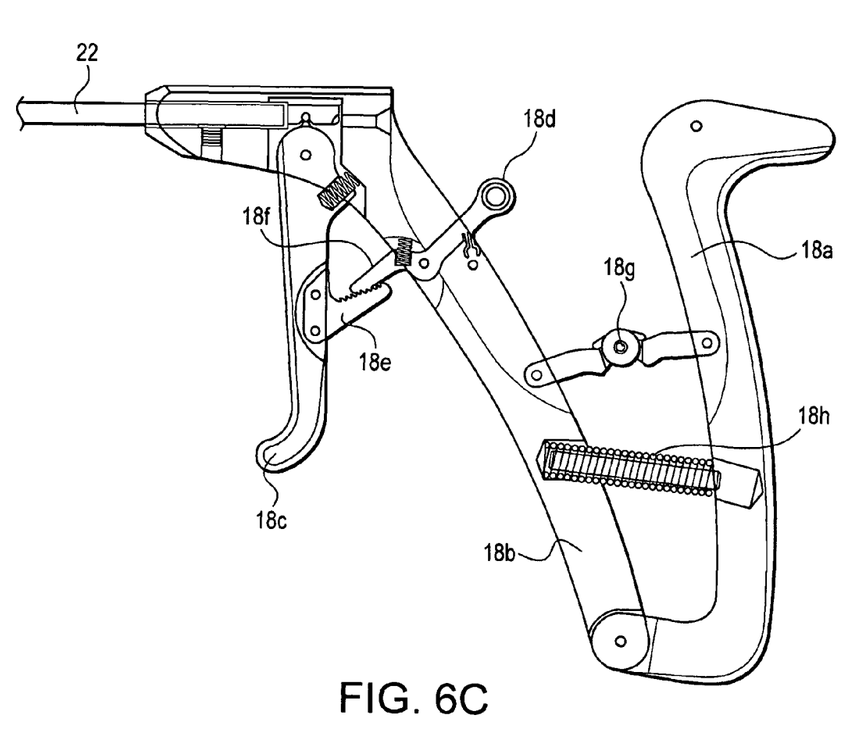
Figure 7A:
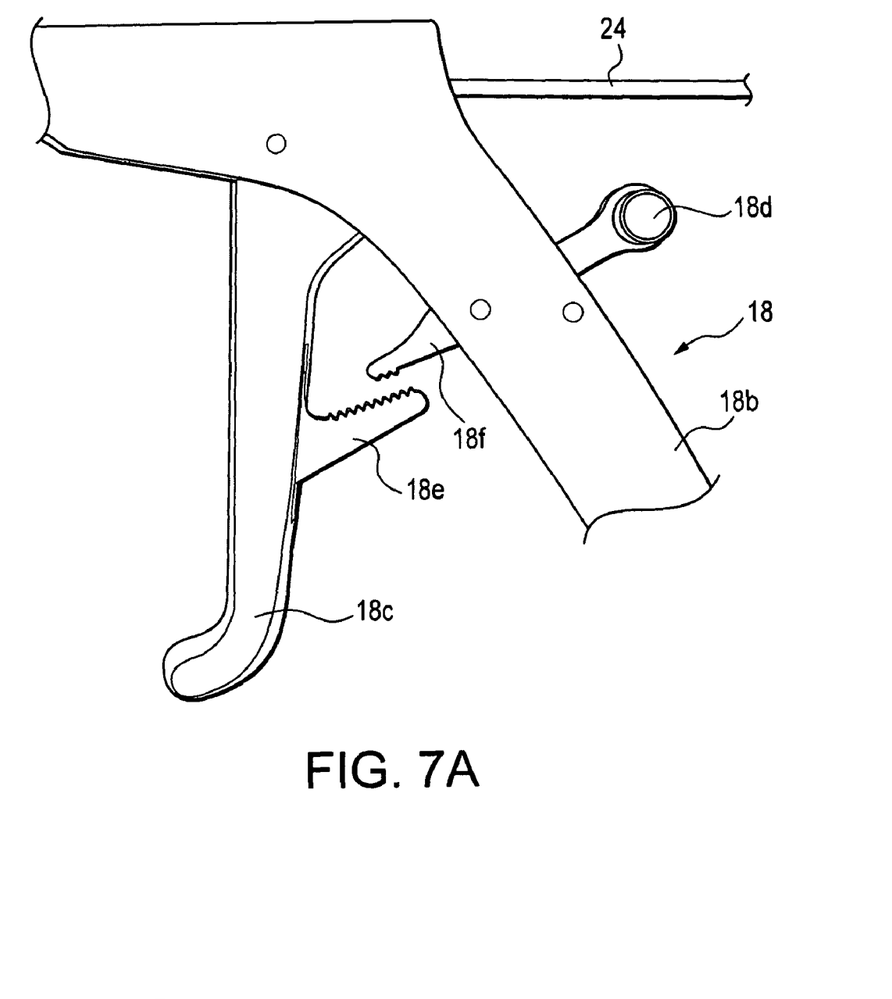
FIG. 7A-7C illustrate a side elevation view of the proximal and distal sides of the suture passing instrument when the ratchet of the suture passing instrument is disabled, in accordance with the first embodiment of the present invention.
Figure 7B:
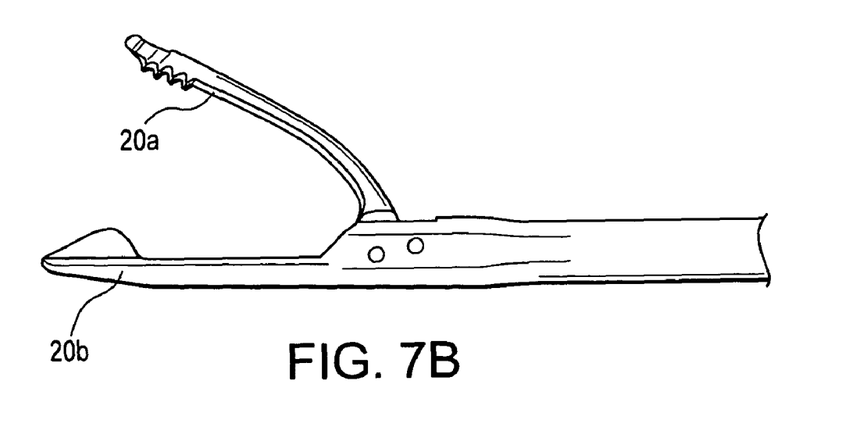
Figure 7C:
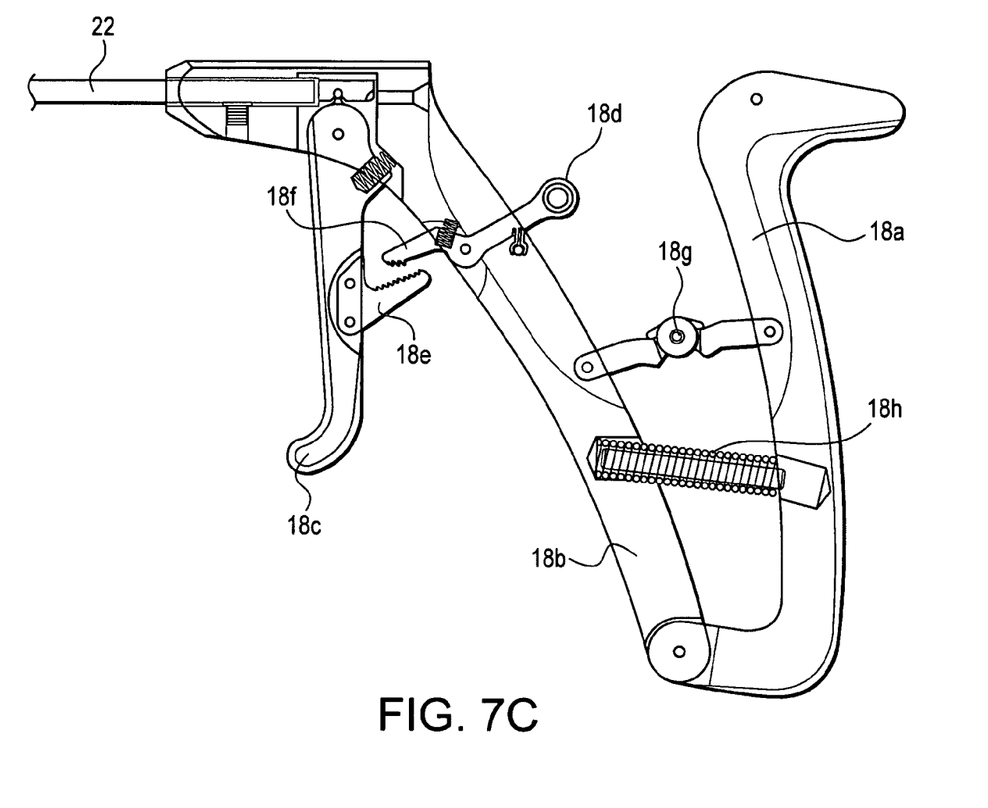

The movement of the upper jaw 20a with respect to the lower jaw 20b is controlled by the handle assembly 18, as shown in FIGS. 6A-6C and 7A-7C. The upper jaw 20a and the lower jaw 20b are together when the finger lever 18c is at a position closest to the distal end 18b of the handle and the ratchet 18e is secured to the hook 18f on the releaser 18d, as shown in FIGS. 6A-6C. The upper jaw 20a moves away from the lower jaw 20b when the ratchet 18e on the finger lever 18c is disenabled from the hook 18f and the finger lever 18c is moved toward its default position, as shown in FIGS. 7A-7C.

FIGS. 8A-8F illustrate a method of use of the suture passing instrument 10. In a first step of suturing using the suture passing instrument 10, referring to FIG. 8A, a needle 24 is loaded into the cannulation 18k on the proximal end of the shaft 16 of the suture passing instrument 10. The slot 24f (FIG. 4B) on the proximal end 24a (FIG. 6A) of the needle 24 is engaged securely into a cross pin 18m (FIG. 3B) on the proximal end 18a of the suture passing instrument's 10 handle. The needle 24 facilitates passing the suture 26 (FIG. 8B) through the tissue.

Figures 8A, 8A:
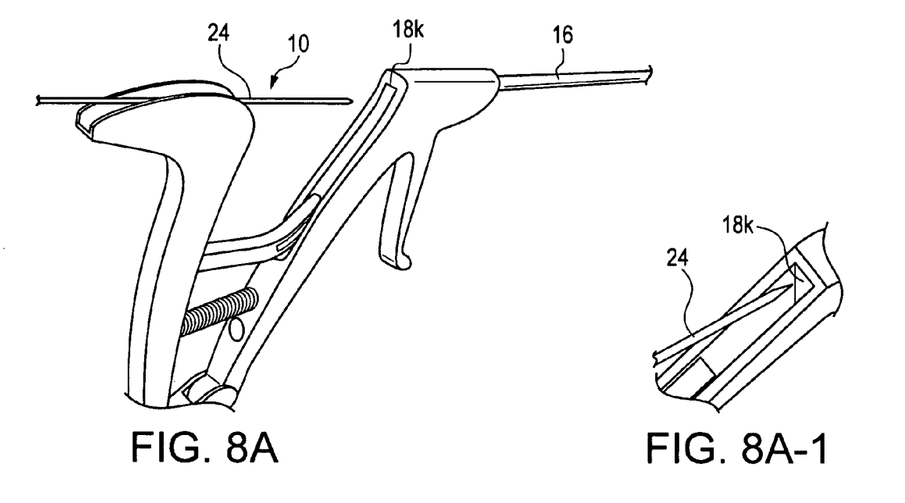
FIGS. 8A-8G illustrate a method of use of the suture passing instrument, in accordance to a second embodiment of the present invention.
Figure 8B:
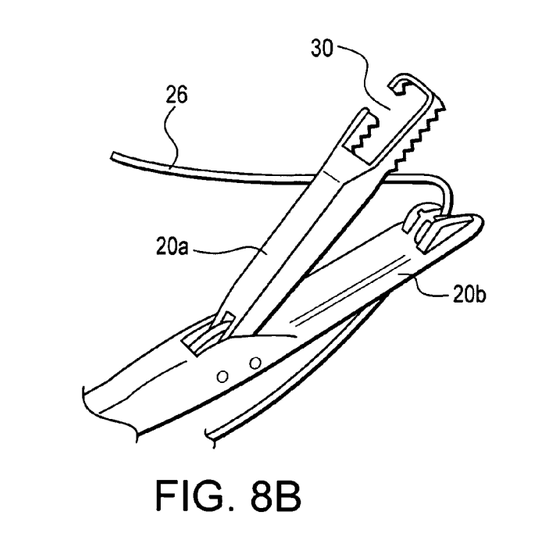
Figure 8B:
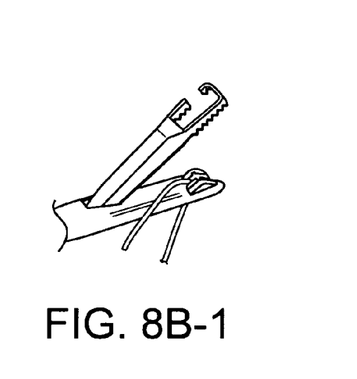

Referring to FIG. 8B, 1-2 inches of suture 26 is loaded into the wedge, slot or groove 42 (FIG. 2) on the lower jaw 20b of the suture passing instrument 10. The suture 26 should snap as it fully engages into the lower jaw 20b.

Figure 8C:
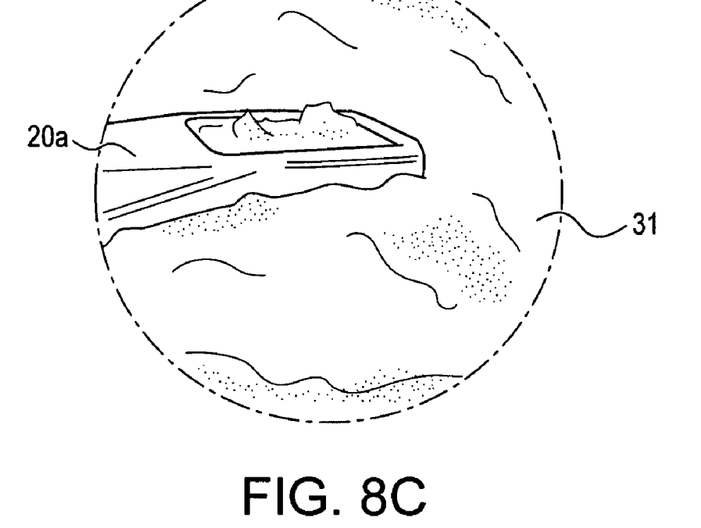

Using the finger lever 18c (FIG. 7A) on the suture passing instrument 10, the upper jaw 20a and the lower jaw 20b are held together, and the suture passing instrument 10 (FIG. 8A) is advanced into the subacromial space, as shown in FIG. 8C. The upper jaw 20a is then disengaged from the lower jaw 20b (FIG. 7A) by releasing the finger lever 18c (FIG. 7A) and a desired bite of tissue 31 is grasped.

Figure 8D:
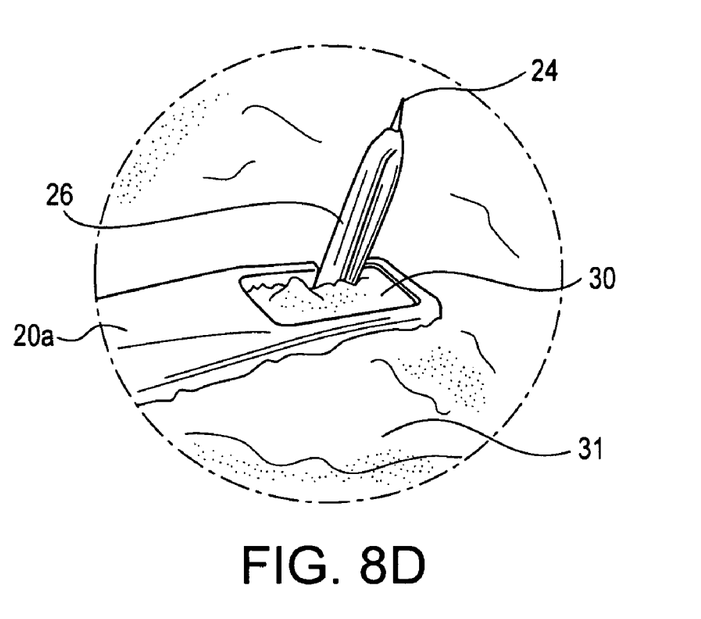
Figure 8E:
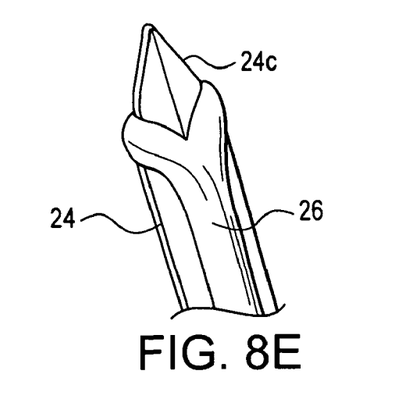

Referring to FIG. 8D, with the jaws closed around the tissue 31, the needle 24 is advanced distally such that the needle 24 exits the opening 23a (FIG. 4) on the lower jaw 20b (FIG. 4). The pointed tip 24c of the needle 24 then pierces partly through the suture and carries the suture 26, as shown in FIG. 8E. The needle 24 and the suture 26 are advanced distally using the handle assembly 18 (FIG. 7A) to advance the suture 26 through the tissue 31.

Figure 8F:
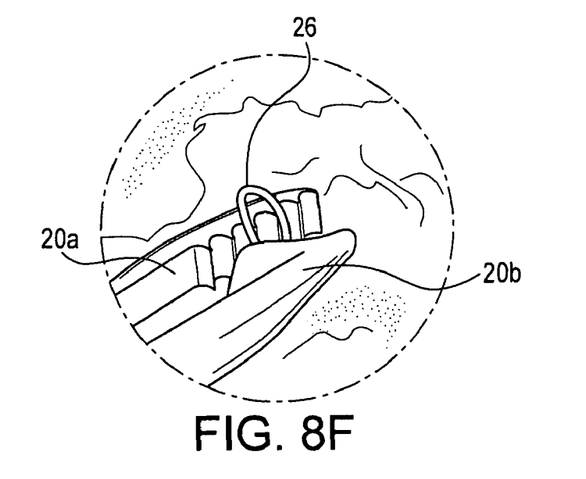
Figure 8G:
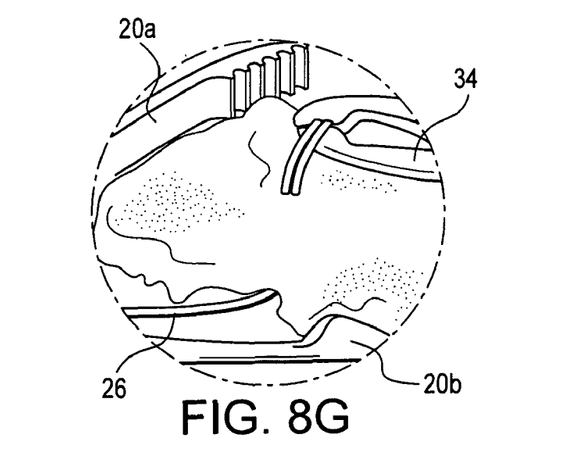

Finally, the suture 26 is retrieved with a suture retriever or tissue grasper 34, as shown in FIGS. 8F-8G. The suture retriever or tissue grasper 34 may be, for example, a KingFisher™ Suture Retriever/Tissue Grasper AR-13970SR, made by Arthrex, Inc., Naples, Fla.

Figure 9:
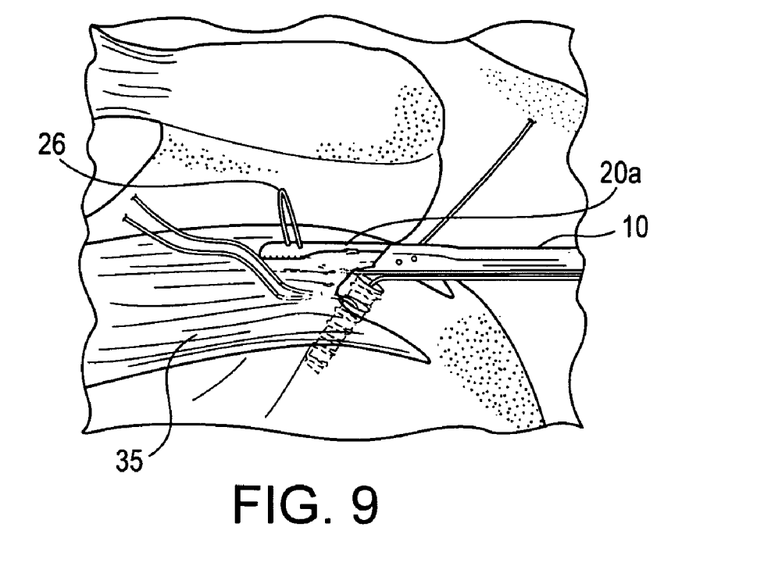
FIG. 9 illustrates a method of use of the suture passing instrument, in accordance to a third embodiment of the present invention.

FIG. 9 further illustrates a method for suturing a tissue using the suture passing instrument 10 of the present invention. In this method, the suture passing instrument 10 is used in a rotator cuff repair. The suture passing instrument 10 loaded with a suture 26 is advanced into the acromion to grab the torn rotator cuff 35. The curve-shaped upper jaw 20a of the suture passing instrument 10 helps in grabbing thick tissues, as shown in FIG. 9.

Figure 10A:
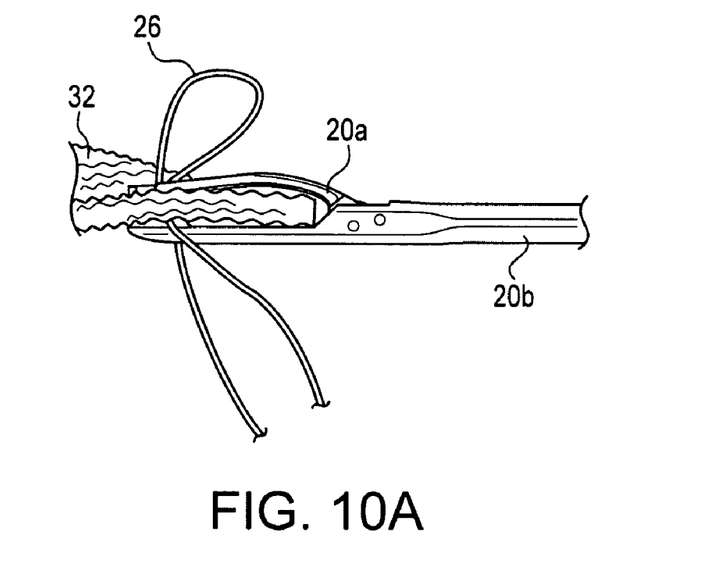
FIGS. 10A-10C illustrate a method of suturing a prototype tissue using the suture passing instrument of the present invention, showing the advantages of the humpback jaw design.
Figure 10B:
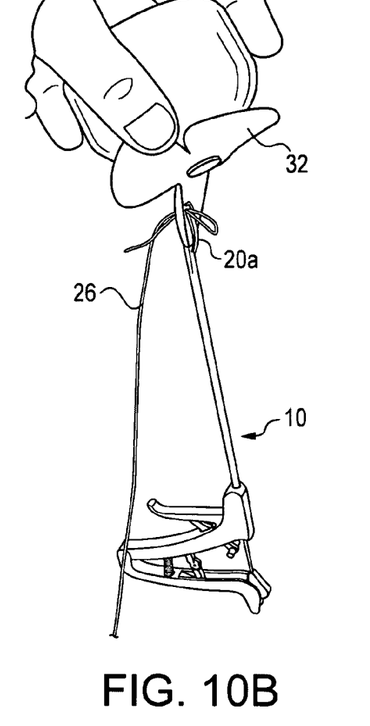
Figure 10C:
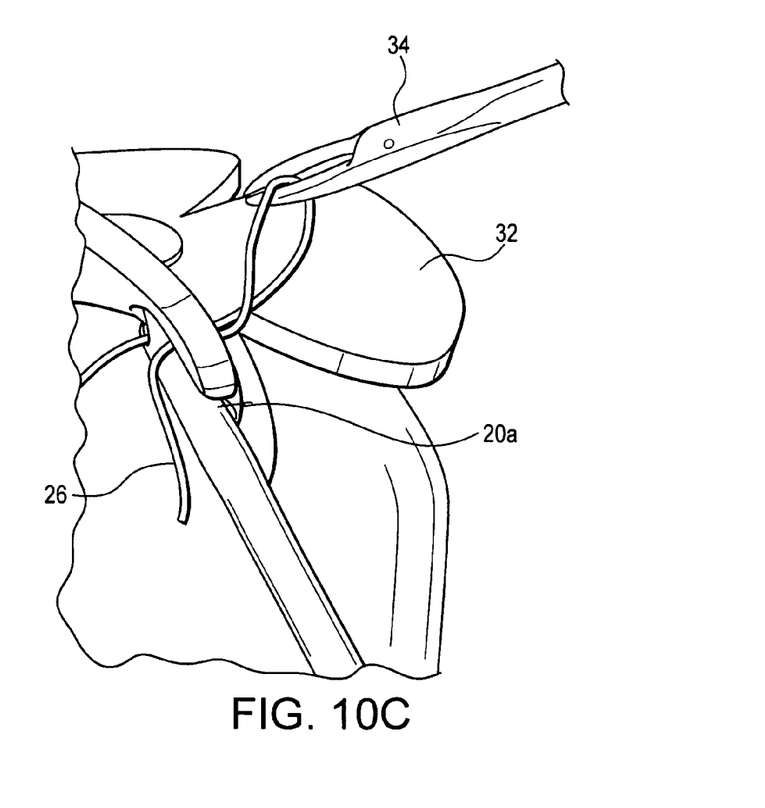

FIGS. 10A-10C further illustrate a method for suturing a tissue 32 using the suture passing instrument 10 of the present invention, showing the advantages of the humpback jaw design. In a first step of suturing using the suture passing instrument 10, a suture 26 is secured in place on the lower jaw 20b for engagement with a flexible needle 24 (not shown). The handle assembly of the suture passing instrument 10 is used to close the upper and lower jaws 20a, 20b and to grasp a desired bite of the prototype tissue 32 using the jaws 20a, 20b. The suture 26 is then engaged with the needle 24. The humpback-shaped upper jaw 20a is designed to be parallel with the lower jaw 20b when the tissue 32 is thick, as shown in FIG. 10A.

Referring to FIG. 10B, the surgeon or the user of the suture passing instrument 10 may release the suture passing instrument 10 from his or her hand. The suture 26 is then grabbed using a grasper or a retriever 34 from an accessory portal, as shown in FIG. 10C. The upper jaw 20a is then released by disabling the ratchet (not shown) and the suture 26 is then retrieved.

Although the pair of jaws in the present application are referred to as upper and lower jaws 20a, 20b in the preferred embodiments, it is to be expressly understood that the jaws may also be provided sideways or in any other configuration suitable for use in surgical procedures.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed is:

1. A method of passing suture through tissue, comprising:
   providing a suture passing instrument, the suture passing instrument comprising:
      an shaft having a distal end and a proximal end, the proximal end having a cannulation to receive a needle;
      a bottom jaw mounted to the distal end of the shaft, the bottom jaw having a groove to secure a suture, a channel for receiving the needle, and an opening in its distal end to allow the needle to pass therethrough;
      a top jaw mounted to the distal end of the shaft and pivotally connected to the bottom jaw such that the top jaw is moveable with respect to the bottom jaw member, and the top jaw being humpback-shaped with a curvature so that the top jaw is parallel to the bottom jaw when grasping tissue;
      a hand assembly comprising a handle and a ratchet-like mechanism, the ratchet-like mechanism including a finger lever with a ratchet and a releaser with a hook;
   mounting a needle in the suture passing instrument by sliding the needle through a cannulation in a proximal end of the shaft such that a distal end of the needle is on the distal end of the shaft;
   loading a suture into the bottom jaw;
   closing the top and bottom jaws and advancing the suture passing instrument into a subacromial space; opening the top jaw by moving the finger lever subsequent to disengaging the ratchet and the hook, and grasping a desired bit of tissue using the top and bottom jaws; closing the top and bottom jaws by using the finger lever; advancing the needle and suture through the tissue; and retracting the needle and retrieving the suture using a retriever or grasper; wherein the step of advancing the needle and suture through the tissue further comprises: advancing the needle by pushing proximal and distal ends of the handle toward each other until the needle exits the opening on the bottom jaw and advances toward the top jaw; piercing the suture with a tip of the needle and firmly holding the suture in the needle; and advancing the needle and the suture through the tissue such that the needle and the suture pass through a channel at a distal end of the top jaw.

2. The method of claim 1, wherein the needle is a nitinol needle.

3. The method of claim 1, wherein the top jaw further comprises a channel at its distal end to allow the needle and the suture to pass therethrough.

4. The method of claim 1, wherein the suture is a braided suture comprising a plurality of high strength fibers.

* * * * *